US009181093B2

(12) United States Patent
Karandikar et al.

(10) Patent No.: US 9,181,093 B2
(45) Date of Patent: Nov. 10, 2015

(54) TWO PART OXYGEN GENERATING SYSTEM

(75) Inventors: Bhalchandra M. Karandikar, Beaverton, OR (US); Sunita J. Macwana, Tigard, OR (US); Zhongju Liu Zhao, Sherwood, OR (US)

(73) Assignee: Avent, Inc., Alpharetta, GA (US)

( * ) Notice: Subject to any disclaimer, the term of this patent is extended or adjusted under 35 U.S.C. 154(b) by 167 days.

(21) Appl. No.: 13/555,336

(22) Filed: Jul. 23, 2012

(65) Prior Publication Data
US 2013/0028810 A1 Jan. 31, 2013

Related U.S. Application Data

(60) Provisional application No. 61/513,126, filed on Jul. 29, 2011.

(51) Int. Cl.
| | | |
|---|---|---|
| *B65D 83/68* | (2006.01) | |
| *A61K 8/02* | (2006.01) | |
| *A61K 8/04* | (2006.01) | |
| *A61K 8/19* | (2006.01) | |
| *A61K 8/22* | (2006.01) | |
| *C01B 13/02* | (2006.01) | |
| *A61Q 19/08* | (2006.01) | |
| *A61K 8/18* | (2006.01) | |
| *A61L 2/16* | (2006.01) | |
| *A61L 2/20* | (2006.01) | |
| *A61L 12/08* | (2006.01) | |
| *A61L 12/12* | (2006.01) | |
| *B01J 8/18* | (2006.01) | |
| *B01J 23/34* | (2006.01) | |

(52) U.S. Cl.
CPC ........... *C01B 13/0214* (2013.01); *A61K 8/0241* (2013.01); *A61K 8/046* (2013.01); *A61K 8/19* (2013.01); *A61K 8/22* (2013.01); *A61Q 19/08* (2013.01); *A61K 2800/22* (2013.01); *A61K 2800/413* (2013.01); *A61K 2800/882* (2013.01)

(58) Field of Classification Search
CPC ............ B01J 8/00; B01J 19/00; B01J 35/023; B01J 4/002; B01J 19/0066; B01J 19/26; B01J 2523/00; B01J 2523/023; B01J 2523/54; B01J 2523/68; B01J 2523/842; B01J 2523/3712; B01J 8/18; B01J 23/00; B01J 23/16; B01J 23/32; B01J 23/34; B01J 2208/02; B01J 2208/023; B01J 2208/024; B01J 2208/026; A01N 59/00; A01N 37/16; C07C 263/10; C07C 67/03; C01B 13/0207; B65D 83/14; B65D 83/68; B65D 83/682; B65D 83/685; A61L 2/16; A61L 2/20; A61L 2/208; A61L 2209/20; A61L 2209/21; A61L 2209/211; A61L 12/08; A61L 12/12; A61L 12/124; A61K 8/02; A61K 8/0241; A61K 8/04; A61K 8/046; A61K 8/18; A61K 8/19; A61K 8/22; A61K 2800/20; A61K 2800/22; A61K 2800/40; A61K 2800/41; A61K 2800/413; A61K 2800/80; A61K 2800/88; A61K 2800/882; A61Q 19/08
USPC ........... 422/129, 211, 224; 423/579
See application file for complete search history.

(56) References Cited

U.S. PATENT DOCUMENTS

| | | | |
|---|---|---|---|
| 2,746,249 A | 5/1956 | Bichowsky et al. | |
| 3,931,912 A | 1/1976 | Hsiung | |
| 4,969,881 A | 11/1990 | Viesturs | |
| 5,477,672 A * | 12/1995 | Tsujikado et al. | 60/39.462 |
| 5,792,090 A | 8/1998 | Ladin | |
| 6,293,433 B1 | 9/2001 | Joulia | |
| 6,322,798 B1 | 11/2001 | Candau et al. | |
| 6,333,093 B1 | 12/2001 | Burrell et al. | |
| 6,458,109 B1 | 10/2002 | Henley et al. | |
| 6,767,342 B1 | 7/2004 | Cantwell | |
| 7,160,553 B2 | 1/2007 | Gibbins et al. | |
| 7,638,470 B2 * | 12/2009 | Coke et al. | 510/109 |
| 2003/0232114 A1 | 12/2003 | Dekleva | |
| 2004/0086453 A1 | 5/2004 | Howes | |
| 2005/0085403 A1 | 4/2005 | Larsen et al. | |
| 2005/0232953 A1 | 10/2005 | Barnikol et al. | |
| 2006/0030900 A1 | 2/2006 | Eckert | |
| 2006/0121101 A1 | 6/2006 | Ladizinsky | |
| 2007/0031348 A1 | 2/2007 | Staeb et al. | |
| 2007/0057082 A1 * | 3/2007 | Mc Gloughlin et al. | 239/11 |
| 2007/0166339 A1 | 7/2007 | Gupta | |
| 2007/0178163 A1 * | 8/2007 | Kodas et al. | 424/489 |
| 2009/0202617 A1 | 8/2009 | Ward et al. | |
| 2009/0258841 A1 | 10/2009 | Murphy et al. | |

(Continued)

FOREIGN PATENT DOCUMENTS

| | | |
|---|---|---|
| DE | 2 239 690 A1 | 2/1973 |
| DE | 2 534 315 A1 | 2/1976 |

(Continued)

OTHER PUBLICATIONS

Co-pending U.S. Appl. No. 13/555,332, filed Jul. 23, 2012, by Karandikar et al. for "Indicator for Oxygen Generation.".

Wekesa, Moses and Yonghao Ni, "Mechanism of Hydrogen Peroxide Decomposition by Manganese Dioxide," Tappi Journal, vol. 2, No. 9, Sep. 2003, pp. 23-26.

Li, Yali et al., "Gold Nanoparticles Mediate the Assembly of Manganese Dioxide Nanoparticles for H2O2 Amperometric Sensing," Electrochimica Acta, Elsevier Science Publishers, vol. 55, No. 18, Jul. 15, 2010, pp. 5123-5128.

Li, Jun et al., "Nickel Foam-Based Manganese Dioxide-Carbon Nanotube Composite Electrodes for Electrochemical Supercapacitors," Journal of Power Sources, Elsevier, vol. 185, No. 2, Dec. 1, 2008, pp. 1569-1574.

Luo, Yonglan, "Preparation of MnO2 Nanoparticles by Directly Mixing Potassium Permanganate and Polyelectrolyte Aqueous Solutions," Materials Letters, vol. 61, No. 8-9, Mar. 12, 2007, pp. 1893-1895.

(Continued)

*Primary Examiner* — Natasha Young
(74) *Attorney, Agent, or Firm* — Dority & Manning, P.A.

(57) ABSTRACT

There is provided a two part spray for the liberation and delivery of oxygen through the use of a first part that is a peroxide-containing solution and a second part that is a nanoparticle manganese dioxide catalyst. When the two parts are mixed together, the ensuing reaction results in the liberation of oxygen.

16 Claims, No Drawings

(56) References Cited

U.S. PATENT DOCUMENTS

| | | |
|---|---|---|
| 2010/0035798 A1 | 2/2010 | Sen et al. |
| 2010/0112087 A1 | 5/2010 | Harrison et al. |
| 2010/0196746 A1* | 8/2010 | Koyanaka ............... 429/50 |
| 2010/0255162 A1 | 10/2010 | Becraft et al. |
| 2011/0015565 A1 | 1/2011 | Hursey |
| 2011/0140038 A1* | 6/2011 | Presley et al. ............ 252/187.31 |
| 2013/0065752 A1* | 3/2013 | Arndt et al. ................. 502/324 |

FOREIGN PATENT DOCUMENTS

| | | |
|---|---|---|
| GB | 2 376 185 A | 12/2002 |
| GB | 2438673 A * | 12/2007 |
| WO | WO 94/21323 A1 | 9/1994 |
| WO | WO 95/00436 A1 | 1/1995 |
| WO | WO 02/060458 A2 | 8/2002 |
| WO | WO 2009/031788 A1 | 4/2008 |
| WO | WO 2008/131070 A1 | 10/2008 |
| WO | WO 2009/127058 A1 | 10/2009 |

OTHER PUBLICATIONS

Nam, Ho-Seong et al., "Supercapacitive Properties of a Nanowire-Structured MnO2 Electrode in the Gel Electrolyte Containing Silica," Electrochimica Acta, Elsevier Science Publishers, vol. 55, No. 25, Oct. 30, 2010, pp. 7443-7446.

Wang, Shufen et al., "One-step Synthesis of Manganese Dioxide/Polystyrene Nanocomposite Foams via High Internal Phase Emulsion and Study of Their Catalytic Activity," Colloid and Polymer Science, vol. 288, No. 9, May 16, 2010 pp. 1031-1039.

Xu, Mao-Wen et al., "Mesoporous Amorphous MnO2 as Electrode Material for Supercapacitor," Journal of Solid State Electrochemistry, vol. 11, No. 8, Jan. 10, 2007, pp. 1101-1107.

Yu, Peng et al., "Preparation and Pseudo-Capacitance of Birnessite-Type MnO2 Nanostructures via Microwave-Assisted Emulsion Method," Materials Chemistry and Physics, Elsevier, vol. 118, No. 2-3, Dec. 15, 2009, pp. 303-307.

* cited by examiner

TWO PART OXYGEN GENERATING SYSTEM

This application claims the benefit of priority from U.S. Provisional Application No. 61/513,126 filed on Jul. 29, 2011, the contents of which are incorporated herein by reference.

BACKGROUND

The present disclosure relates to the generation oxygen for use in cosmetic formulations.

The lack of oxygen, i.e. hypoxia, is commonly experienced by people in their extremities as they get older due to poor blood circulation as well as by those with conditions such as diabetes. Studies have also shown below normal, low oxygen tension in the skins of older people. This often leads to poor skin health and an excessive presence of visible conditions such as wrinkles, dryness and lower skin elasticity. Over the years, cosmetic manufacturers have introduced skin formulations with a large variety of ingredients such as emollients, exfoliators, moisturizers etc., to retard these age related effects and improve and maintain skin health. Attacking the problem of low oxygen directly has not been generally practiced.

The delivery of oxygen to the skin for common use is a technological challenge, since oxygen is quite reactive and unstable. High concentrations of oxygen could not be provided for home use because of this instability. Oxygen can, however, be provided in the form of a peroxide and a peroxide decomposition catalyst per US patent publication 2006/0121101 to Ladizinsky. This publication provides such a treatment for intact skin through the use of a dressing that is applied to an area of the skin. The dressing generally has a rupturable reservoir containing an aqueous hydrogen peroxide composition and a hydrogel layer having a peroxide decomposition catalyst. Unfortunately the catalytic decomposition of hydrogen peroxide to oxygen is quite rapid and so the dressing has a layer that is impermeable to oxygen on the outside so that the oxygen is held against the skin for the maximum time possible. While this dressing is useful for small areas of the skin, it should be clear that it is unworkable for large areas or irregularly shaped areas of skin.

Alternatively, Devillez (U.S. Pat. No. 5,736,582) proposes the use of hydrogen peroxide in the place of benzoyl peroxide in skin treatment compositions that also contain solvents for hydrogen peroxide. This allows the hydrogen peroxide to stay below a level that will damage the skin and to stay in solution in greater concentrations. A solvent such as dimethyl isosorbide along with water is taught as being effective. No peroxide decomposition catalyst is present. Unfortunately, no data on oxygen concentration or generation are given, nor is the time required for oxygen liberation. While this method appears to be an advance over non-oxygen containing compositions, the lack of data makes it difficult to make objective judgments on the overall effectiveness of this approach. Given the concentrations of peroxide, however, it is doubtful that significant volumes of oxygen were generated.

There is a need for an easy-to-use way of applying oxygen to the skin. Such a method and/or product should have relatively few components and be intuitive to use, without the need for special dressings or other awkward requirements. A product that may be used in a manner similar to known products would be most readily accepted by the consumer.

SUMMARY

The problem discussed above has found a solution to a large degree in the present disclosure, which describes the use of manganese dioxide ($MnO_2$) nanoparticles which, when added into the peroxide carrying part of the topical composition, generate oxygen rapidly and effectively. Manganese dioxide particles that are not nanoparticles fail to exhibit this behavior.

A two part spray wherein one part has manganese dioxide nanoparticles with an average size between about 1 and 1000 nanometers and the other part contains hydrogen peroxide performs well in delivering oxygen to the skin.

The disclosed topical compositions having a catalyst containing part and an oxygen precursor part may be either aqueous, non-aqueous or a mixture of the two e.g. emulsions. Both oil in water (o/w) or water in oil (w/o) compositions are encompassed by the present disclosure. To impart additional cosmetically desirable properties, the component compositions (with catalyst and/or oxygen precursor) may contain other ingredients such as natural or synthetic polymers, moisturizers, humectants, viscosity modifiers, emollients, texture enhancers, UV blocking agents, colorants, pigments, ceramics (fumed silica, titanium dioxide, natural and synthetic clays), antioxidants, fragrances etc.

DETAILED DESCRIPTION

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

The application of oxygen to the skin can help to alleviate a number of problems brought on by ageing such as poor skin health and an excessive presence of visible conditions such as wrinkles, dryness and lower skin elasticity. Oxygen applied to the skin can help to retard these age related effects and improve and maintain skin health.

Applying oxygen to the skin topically through the application of a liquid or foam composition is a convenient, easy and quick method of delivering the desired benefits discussed above. A two part formulation as disclosed herein helps to ensure that the oxygen is available for use and has not been lost during storage. Delivering oxygen in the form of a peroxide helps ensure the oxygen remains present until it is needed, since oxygen is a fugitive substance that is highly reactive. Catalyzing the peroxide with manganese dioxide to produce oxygen on-demand allows the consumer to choose when the oxygen is delivered. It is important with two part systems, however, that the two components be thoroughly mixed to ensure that the maximum amount of oxygen is released to deliver the maximum benefit.

Nanoparticle sized manganese dioxide means particles in the range of from 1 to 1000 nanometers, more desirably from 5 to 500 nanometers and still more desirably from 50 to about 300 nanometers. The base solution may be a liquid, gel, foam or emulsion of oil in water or water in oil. Examples of base solutions are given below. The concentration of manganese dioxide in the base solution may be between 500 and 10000 ppm, more desirably between about 900 and 5000 ppm, and the concentration of hydrogen peroxide generally from a positive amount to about 3 weight percent.

Once the base solution containing the nanoparticle manganese dioxide has been made, it may be stored for later use without deterioration of the manganese dioxide. Likewise the second component, the hydrogen peroxide, may be stored separately without deterioration under the proper conditions. Once it is desired to liberate the oxygen from the hydrogen peroxide and treat the skin, the two components should be thoroughly mixed to release the maximum amount of oxygen.

A delivery system for the two components may be a spray bottle that contains separate reservoirs and that mixes the two components in a nozzle as they leave the bottle. The two part dispensers also known as dual chamber dispensers are available commercially from, for example, New High Glass Inc. of Miami, Fla. (see www.newhighglass.net). The company information cited here is for illustrative purpose only. The suitability of the two part compositions of the present disclosure for application is not limited to this company's dispensers only but other company dispensers may be used so long they meet the functional requirements. The two part dispensers wherein the proportions of the two parts can be adjusted by a user are also suitable for use with the present disclosure. There also are similar dispensers for combining two parts and forming aerosols or sprays. One such dispenser is available from Lindal Group of Germany (www.lindalgroup.com) and identified as "bag-in-bag" with "bag on valve' system. Published patents (see U.S. Pat. No. 5,402,916 and references cited therein are incorporated herein in their entirety) and describe such two part spray systems.

Example 1

Preparation of Manganese Dioxide Nanoparticles 1.87 gram of Poly-Allylamine Hydrochloride (PAH, 15,000 Mw, 93.5 g/mol, from Sigma-Aldrich) was dissolved in 50 mL of de-ionized (Di) water to prepare 0.4M solution. 0.79 gram of Potassium Permanganate (KMnO4) (158.03 g/mol, from Riedel-de-Haen) was dissolved in 50 mL of Di water to give 0.2M solution. Both solutions were mixed in a glass beaker (250 mL capacity) at room temperature with a magnetic stirrer. Upon mixing, the color of the mixed solutions began to change from dark red to dark brown indicating the reduction reaction (KMnO4 to manganese dioxide) was taking place. The solution in the beaker was stirred overnight. Completion reduction to manganese dioxide was confirmed by a single absorption peak at ~350 nm in the UV-VIS spectrum of the final solution. The final manganese dioxide nanoparticles solution had approximately 4300 ppm by weight manganese dioxide. This solution was diluted in Di water to a 1000 ppm stock solution for further use.

Example 2

Testing of Two Part Aqueous Formulations for on Demand Oxygen Generation

The prototype two part formulations were prepared to demonstrate the feasibility of an on demand oxygen generating product. Part one consisted of 0.9% w/w hydrogen peroxide made from a 35% w/w hydrogen peroxide solution (Spectrum HY115; New Brunswick, N.J.). Part two with varying concentrations (100 ppm, 75 ppm, 50 ppm and 25 ppm by weight) of Manganese dioxide nanoparticle (manganese dioxide NP) was diluted from a stock solution of 1000 ppm per Example 1. Parts one and two were combined in a 1:1 ratio by volume to decompose hydrogen peroxide to oxygen. Test samples were made by carefully combining the same volume (2 ml) aliquots of manganese dioxide NP solution (varying the manganese dioxide concentration) in different 5 ml Falcon tubes with 2 ml aliquots of 0.9% aqueous hydrogen peroxide. A control sample was made by combining 2 ml of 0.9% aqueous hydrogen peroxide and 2 ml of Di water. The color of part two (varying concentrations of manganese dioxide NP) before the addition of part one and the color of the mix (part 1 and part two combined) were noted (description as in Table 1). All test samples and the control were assayed for remaining hydrogen peroxide immediately after combining the two parts at 0-2 mins and at 60 mins. For assay purposes, an aliquot (150 microliter) of the mixture was tested for residual peroxide using the Horseradish Peroxidase (HRP) Assay (described in Example 3). Note that the decomposition reaction of hydrogen peroxide was very rapid and formed a lot of oxygen bubbles, causing effervescence. Separately, using identically made test samples, the oxygen flux through a polyethylene membrane into saline was measured (as described in Example 4). As seen in Table 1, nanosized manganese dioxide (manganese dioxide NP) at 75 ppm and higher completely decomposed aqueous 0.9% hydrogen peroxide. The color of the manganese dioxide NP solution at 50 ppm or less though light yellow was aesthetically acceptable. Interestingly, the combined solutions (Parts 1 and 2) became colorless except when the initial manganese dioxide NP was 100 ppm. This result was unexpected as this observation has not been reported in the published literature, to the best of our knowledge.

TABLE 1

| Amount of manganese dioxide NP (ppm) | Color of manganese dioxide NP only (ppm) | Percentage of 0.9% hydrogen peroxide decomposition Avg. (n = 3) | | Color of 0.9% hydrogen peroxide + manganese dioxide NP | $O_2$ flux...2/ |
|---|---|---|---|---|---|
| | | 0 min | 60 min | | min |
| 100 | Light brown | 100 | 100 | Light yellow tint | 0.376 |
| 75 | Light brown | 46 | 100 | colorless | 0.371 |
| 50 | Light yellow | 36 | 46 | colorless | 0.214 |
| 25 | Light yellow | 11 | 15 | colorless | 0.100 |

0.9% hydrogen peroxide decomposition: ((control − sample)/control) * 100
Control: 0.9% hydrogen peroxide (No manganese dioxide NP)
Sample: 0.9% hydrogen peroxide + manganese dioxide NP (varying ppm)

Example 3

The Horseradish Peroxidase Assay Employed for Measuring Residual Hydrogen Peroxide in Test Samples and Controls Horseradish peroxidase (HRP) catalyzes the reaction of hydrogen peroxide, oxidizing the chromogenic substrate o-phenylenediamine (OPD). The rate of peroxide decomposition can be measured spectrophotometrically at 490 nm. The assay described in detail elsewhere (see reference below) was modified for the present work.

REFERENCE

Formera S, Walde P., Spectrophotometric quantification of horseradish peroxidase with o-phenylenediamine. Anal Biochem. 2010 Dec. 15; 407(2):293-5. Epub 2010 Aug. 6. Department of Materials, ETH Zürich, CH-8093 Zürich, Switzerland.

Example 4

Measurement of Oxygen Flux from a Two Part Aqueous Formulation

The rate of hydrogen peroxide decomposition listed in the Table 1 (Example 2) was corroborated by measuring the oxygen flux at 25 C. Part one (0.9% hydrogen peroxide portion) and Part two (manganese dioxide NP) were freshly prepared and mixed in a 1:1 ratio; 1.2 mL of 0.9% aqueous hydrogen peroxide with 1.2 mL of manganese dioxide NP was directly mixed onto the polyethylene (PE) membrane (~25 micron thick) of a Franz cell. The membrane acted as a flexible wall of the Franz cell that was filled with air saturated saline solution. The cell was fitted with a dissolved oxygen measuring probe (Foxy® probe from Ocean Optics, Fla.). The dissolved oxygen probe allowed the monitoring of oxygen uptake by the saline solution in ppm over time. After the mix was placed in the cell, the oxygen concentration in the saline was monitored. After an initial time lag of ~5 minutes, the oxygen concentration began to increase linearly with time over the next 60 minutes. Using the linear slope value, the oxygen flux ($mg/cm^2/min$) was calculated using a simple mathematical model. The oxygen flux values measured for various samples are listed in the Table 1. As one can see, an increase in flux corresponded with the increased peroxide decomposition with increasing concentrations of manganese dioxide NP. The highest flux value ~0.37 was very close to the flux value of ~0.4 observed separately for an aqueous solution saturated with oxygen at 1 atmosphere and 25 C.

The Franz Cell Chamber

The Franz Cell chamber is an in vitro skin permeation assay frequently used in formulation development. The Franz Cell apparatus consists of two primary chambers separated by a membrane. Although animal skin can be used as the membrane, human skin or other membranes such as the polyethylene used above are suitable. The test product is applied to the membrane via the top chamber. The bottom chamber contains fluid from which samples are taken at regular intervals for analysis. This testing determines the amount of active that has permeated the membrane at each time point. The chamber is maintained at a constant temperature. Depending on the vehicle, the rate of permeation as determined via Franz cell analysis can vary significantly (perhaps from 10- to 50-fold).

Example 5

Effect of Co-Catalysts on the Rate of Peroxide Decomposition

Co-catalysts (inorganic bases) like sodium bicarbonate ($Na_2CO_3$) and calcium hydroxide ($Ca(OH)_2$) as low as 0.11M, enhance the decomposition rate of hydrogen peroxide in combination with low concentration levels of manganese dioxide NP. As low as 50 ppm manganese dioxide NP when tested in combination with 0.11M of co-catalyst completely decomposes 0.9% aqueous hydrogen peroxide immediately on-demand (Table 2).

To study the effect of co-catalysts, 2 ml of 0.9% aqueous hydrogen peroxide (Spectrum HY-115) was taken in a 5 ml Falcon tube to which was added 1.9 ml of a particular concentration of manganese dioxide NP and 0.1 ml of 0.11M $Na_2CO_3$. Separately, the same proportions were tested using 0.1 ml of a 0.11M $Ca(OH)_2$ solution. Similarly, each concentration of manganese dioxide NP (25 ppm, 50 ppm, 75 ppm and 100 ppm) was tested separately. A control sample not containing any manganese dioxide NP was assayed as well (data not shown) by mixing 2 ml of 0.9% aqueous hydrogen peroxide (hydrogen peroxide) with 2 ml of Di water. The reaction mix was tested within 2 mins of mixing by HRP assay as described in the earlier example.

TABLE 2

| Amount of manganese dioxide NP (ppm) | $Ca(OH)_2$ | $Na_2CO_3$ | Percentage of 0.9% hydrogen peroxide decomposition Avg. (n = 3) | | $O_2$ flux $ug/cm^2/min$ |
| --- | --- | --- | --- | --- | --- |
| | | | 0 min | 60 min | |
| 0 | | 0.11M | 11 | 18 | 0.150 |
| 25 | 0.11M | | 80 | 96 | 0.228 |
| | | 0.11M | 100 | 100 | 0.398 |
| 50 | 0.11M | | 100 | 100 | 0.204 |
| | | 0.11M | 100 | 100 | Not meas. |
| 75 | 0.11M | | 100 | 100 | Not meas. |
| | | 0.11M | 100 | 100 | Not meas. |

0.9% hydrogen peroxide decomposition: ((control − sample)/control) * 100
Control: 0.9% hydrogen peroxide (No manganese dioxide NP)
Sample: 0.9% hydrogen peroxide + Amount of manganese dioxide NP (ppm) + co-catalyst Clearly, with co-catalyst present in the test samples, 100% hydrogen peroxide decomposition was seen for as low as 25 ppm manganese dioxide (Table 2). In contrast, nearly 4 times as much manganese dioxide (100 ppm) was required to drive the decomposition to completion without the co-catalyst present (see Table 1).

To understand if the co-catalysts caused this catalytic effect through their alkalinity, we measured pH of the test solutions. The data (presented in Table 3) showed the pH of $Ca(OH)_2$ containing solutions ranged between 10.2 and 10.8 and for those that contained $Na_2CO_3$, ranged between 9.9 and 11. Therefore, the catalytic effect was indeed due to the increased alkalinity of the test solutions. While higher than neutral pH affords higher peroxide decomposition, it is generally not desirable in skin care formulations. Preference is for pH to be near neutral or slightly acidic (6 to 7.5).

TABLE 3

| Amount of manganese dioxide NP (ppm) | $Ca(OH)_2$ | $Na_2CO_3$ | pH of the Mix | Percentage of 0.9% hydrogen peroxide decomposition Avg. (n = 3) | | $O_2$ flux $ug/cm^2/min$ |
| --- | --- | --- | --- | --- | --- | --- |
| | | | | 0 min | 60 min | |
| 0 | | 0.11M | 9.9 | 11 | 18 | 0.150 |
| 25 | 0.11M | | 10.2 | 80 | 96 | 0.228 |
| | | 0.11M | 11 | 100 | 100 | 0.398 |
| 50 | 0.11M | | 10.8 | 100 | 100 | 0.204 |
| | | 0.11M | 11 | 100 | 100 | Not meas. |
| 75 | 0.11M | | 10.5 | 100 | 100 | Not meas. |
| | | 0.11M | 11 | 100 | 100 | Not meas. |

0.9% hydrogen peroxide decomposition: ((control − sample)/control)*100
Control: 0.9% hydrogen peroxide (No manganese dioxide NP)
Sample: 0.9% hydrogen peroxide + Amount of manganese dioxide NP (ppm) + co-catalyst

Example 6

Effect of Neutral pH on Hydrogen Peroxide Decomposition in the Presence of Co-Catalysts To study the effect of pH on the rate of hydrogen peroxide decomposition near neutral condition (pH 6-7.5), the test solutions with co-catalysts were acidified using 0.1M Hydrochloric acid (HCl) to a pH of 7.5. With varying concentrations of manganese dioxide NP in the presence of co-catalysts, changing the pH from alkaline (Table 3) to neutral (Table 4) slightly decreased the rate of hydrogen peroxide decomposition. Thus, to achieve 100% hydrogen peroxide decomposition under neutral conditions required a higher amount of manganese dioxide NP (75+ ppm) compared to 25 ppm manganese dioxide NP under alkaline conditions. As before, the test solutions in this experiment were assayed for peroxide decomposition by the method of Example 5.

TABLE 4

| Amount of manganese dioxide NP (ppm) | pH of the Mix | Percentage of 0.9% hydrogen peroxide decomposition Avg. (n = 3) | | $O_2$ flux ug/cm2/min |
|---|---|---|---|---|
| | | 0 min | 60 min | |
| 25 | 11 | 100 | 100 | 0.398 |
| | 7.5 | 29 | 78 | 0.203 |
| 50 | 11 | 100 | 100 | Not meas. |
| | 7.5 | 76 | 100 | 0.248 |
| 75 | 11 | 100 | 100 | Not meas. |
| | 7.5 | 85 | 100 | 0.248 |

0.9% hydrogen peroxide decomposition: ((control − sample)/control) * 100
Control: 0.9% hydrogen peroxide (No manganese dioxide NP)
Sample: 0.9% hydrogen peroxide + Amount of manganese dioxide NP (ppm) + co-catalyst Example 7

Effect of Viscosity of Amigel on Hydrogen Peroxide Decomposition

The purpose of this example was to make gel prototypes with varying concentrations of Amigel to examine the effect of viscosity on the hydrogen peroxide decomposition reaction of a two part system. A stock solution of 10% Amigel, a natural biopolymer and a cosmetic ingredient, was prepared. Briefly, 60 gram of Amigel (from Alban Muller) was mixed with 540 gram of DI water at 90 degree Celsius to yield 10% Amigel w/w stock solution. This stock solution was further diluted to prepare a 1.0% w/w, 0.5% w/w and 0.25% w/w Amigel solution.

A two part gel system was prepared with the 1.0% w/w, 0.5% w/w and 0.25% w/w Amigel. The first part was a 0.9% hydrogen peroxide Amigel; 0.64 grams (35%, Spectrum peroxide) was added and mixed into 25 grams of 1.0%, 0.5% and 0.25% w/w Amigel solutions, separately. The second part was the 25 ppm manganese dioxide NP Amigel; 0.145 mL (4300 ppm, stock solution of manganese dioxide NP prepared in Example 1) was added and mixed into 25 grams of 1.0%, 0.5% and 0.25% w/w Amigel solutions separately. To assay the rate of hydrogen peroxide decomposition, 2.0 mL of 0.9% hydrogen peroxide Amigel portion was mixed with 1.9 mL of the 25 ppm manganese dioxide NP Amigel portion to which was added 0.1 mL of co-catalyst (0.11M $Na_2CO_3$). The reaction mix was tested within 2 mins of mixing using the HRP assay as explained in Example 3. Each concentration of 0.9% hydrogen peroxide in 1.0%, 0.5% and 0.25% w/w Amigel was tested separately. Similarly, the 25 ppm manganese dioxide NP in 1.0%, 0.5% and 0.25% w/w Amigel was tested separately.

As can be seen by the results in Table 5, the viscosity had no effect on the hydrogen peroxide decomposition reaction of a two part system.

TABLE 5

| Experimental Detail | Percentage of 0.9% hydrogen peroxide decomposition Avg. (n = 3) | |
|---|---|---|
| | 0 min | 60 min |
| 2 mL 0.9% hydrogen peroxide in 0.25% Amigel + 1.9 mL 25 ppm manganese dioxide NP in 0.25% Amigel + 0.1 mL 0.11M $Na_2CO_3$ | 88 | 100 |
| 2 mL 0.9% hydrogen peroxide in 0.5% Amigel + 1.9 mL 25 ppm manganese dioxide NP in 0.5% Amigel + 0.1 mL 0.11M $Na_2CO_3$ | 88 | 100 |
| 2 mL 0.9% hydrogen peroxide in 1.0% Amigel + 1.9 mL 25 ppm manganese dioxide NP in 1.0% Amigel + 0.1 mL 0.11M $Na_2CO_3$ | 88 | 100 |

0.9% hydrogen peroxide decomposition: ((control − sample)/control) * 100
Control: 0.9% hydrogen peroxide in Amigel (1%, 0.5% or 0.25%) without manganese dioxide NP
Sample: 0.9% hydrogen peroxide (1%, 0.5% or 0.25%) + Amount of manganese dioxide NP (ppm) in Amigel (1%, 0.5% or 0.25%) + 0.11M $Na_2CO_3$ (co-catalyst)

Example 8

Shelf-Life Stability of 0.9% Hydrogen Peroxide (Spectrum HY115) at 25° C. and 40° C.

For any cosmetic formulation, a reasonable stability of one year or more is desired to meet the industry shelf life requirement. This study tested the stability of 0.9% hydrogen peroxide made from a 35% hydrogen peroxide solution (Spectrum HY115; New Brunswick, N.J.). The measure of stability was less than 10% loss from initial concentration in hydrogen peroxide at the end of accelerated test period of 12 weeks at 40° C. Samples maintained at 25 C served as controls.

The testing was done with a sample size of n=3. Briefly, 1.28 mL of 35% Spectrum HY115 peroxide was added to 48.72 mL of Di water to make a 50 mL, 0.9% hydrogen peroxide solution. Three of the 50 mL screw capped tubes with 0.9% hydrogen peroxide were placed in a temperature controlled incubated at 25° C. and the other three tubes with 0.9% hydrogen peroxide were placed in a temperature controlled incubated at 40° C. On Day 0 (day of preparation) each of the tubes was assayed for peroxide content using the HRP assay as described in example 3. Each week the samples at 25° C. and 40° C. were assayed for peroxide content using the HRP assay as described in example 3. The samples aged at 40 C for 12 weeks corresponded to a 2 years' shelf-life. The results are presented in Table 6. Negligible change in hydrogen peroxide concentration in the samples at 25° C. was observed over 12 weeks. But, for the samples at 40° C. a drop in hydrogen peroxide concentration of 20% from initial was seen after 3 weeks. Thereafter, no change was observed through 12 weeks. Considering these samples were experimental in nature, the stability is acceptable.

TABLE 6

| | Percentage (%) Peroxide measured over time (Wks) Avg. (n = 3) | | | | | | | | |
|---|---|---|---|---|---|---|---|---|---|
| Temp ° C. | Day 0 | Wk 1 | Wk 2 | Wk 3 | Wk 4 | Wk 6 | Wk 8 | Wk 10 | Wk 12 |
| 25° C. | 0.876 | 0.94 | 0.956 | 0.946 | 0.936 | 0.915 | 0.887 | 0.922 | 0.912 |
| 40° C. | 1.072 | 1.089 | 0.916 | 0.912 | 0.907 | 0.877 | 0.878 | 0.914 | 0.882 |

Example 9

Shelf-Life Stability of 100 ppm Manganese Dioxide NP at 40° C.

As mentioned in the Example 8, it is important that the manganese dioxide NP containing solution also exhibit its activity over its entire shelf life. This example describes a study done to test the stability of 100 ppm manganese dioxide NP solution at 40° C. We chose 100 ppm solution, as the stability of a high concentration would generally imply a good stability of all solutions less than 100 ppm.

A 50 mL solution of 100 ppm manganese dioxide NP was prepared from the stock solution per Example 1. The 100 ppm manganese dioxide NP solution in a Falcon PP tube was placed in a temperature controlled incubator at 40° C. for 12 weeks. The stability of the manganese dioxide NP solution was measured by its ability to decompose 0.9% hydrogen peroxide solution. At each time point as indicated in Table 7, 0.5 mL of the 100 ppm manganese dioxide NP solution was aliquoted into a 5 mL Falcon tube to which was added 0.9% hydrogen peroxide solution (as prepared in Example 8). A control sample was assayed as well (data not shown); 2 ml of 0.9% aqueous hydrogen peroxide (hydrogen peroxide) was taken in a 5 ml Falcon tube to which was added 2 ml of Di water. The reaction generated rapid effervescence with the release of oxygen within 2 minutes of mixing. The rate of peroxide decomposition with the 100 ppm of manganese dioxide NP was assayed using the HRP assay as described in Example 3.

The results below in Table 7 indicate that the 100 ppm manganese dioxide NP solution maintained at 40° C. was active in decomposing 0.9% hydrogen peroxide; 100% decomposition up to 6 weeks and 94%-98% thereafter up to 12 weeks, which is quite good.

TABLE 7

| Avg. (n = 3) | day 0 | 1 wk | 2 wk | 3 wk | 4 wk | 6 wk | 8 wk | 10 wk | 12 wk |
|---|---|---|---|---|---|---|---|---|---|
| Percentage of 0.9% hydrogen peroxide decomposition | 100% | 100% | 100% | 100% | 100% | 97.02 | 97.65 | 93.99 | 94.78 |

0.9% hydrogen peroxide decomposition: ((control − sample)/control)*100
Control: Just 0.9% hydrogen peroxide (No manganese dioxide NP)
Sample: 0.9% hydrogen peroxide + 100 ppm manganese dioxide NP The experimental work above shows that under alkaline conditions at 25 C, the decomposition of hydrogen peroxide was complete i.e. 100% using as little as 25 ppm manganese dioxide nanoparticle-containing solution. However, when the pH was shifted to a more neutral condition i.e. a pH of about 7-7.5, 75 ppm or greater concentration of manganese dioxide nanoparticles in solution was required to achieve 100% hydrogen peroxide decomposition.

The oxygen flux through a PE membrane (area: 8 cm2) at 25 C was measured from a fresh mixture of hydrogen peroxide (0.9% wt) and manganese dioxide nanoparticles (25 ppm) solution (2.4 gm total). This produced 100% peroxide decomposition and the flux was found to be ~0.38 micrograms of oxygen/cm2/min. This value was comparable to the oxygen flux value obtained for an aqueous solution of oxygen prepared by bubbling pure oxygen gas at 1 atmosphere (0.4 micrograms of oxygen/cm2/min). In contrast, the commercial Sephora gel product gave an oxygen flux of ~0.18 micrograms of oxygen/cm2/min. Note, an aqueous solution in equilibrium with pure oxygen gas at 1 atmosphere and 25 C contains ~40 ppm of dissolved oxygen. In comparison, under ambient air (Total pressure: 1 atmosphere and oxygen partial pressure ~0.2 atmosphere and 25 C), the amount of dissolved oxygen in water is ~8 ppm.

In other words, the aqueous compositions disclosed herein were able to produce supersaturated dissolved oxygen-containing solutions, on demand and were able to deliver oxygen twice as fast as the commercially available Sephora gel product. Due to greater availability of dissolved oxygen in the compositions disclosed herein (~40 ppm versus 8 ppm from an air saturated solution), the compositions should offer a greater therapeutic benefit of oxygen by virtue of faster penetration. The faster penetration is because of an increased driving force or increased differential between the concentration of oxygen in the skin and in the composition.

Example 10

Base Solution as Foam (Prophetic)

A 2 part foam composition for generating O2 is prepared by the modification of the example described in column 3 (lines 65-75) of U.S. Pat. No. 3,423,330. The hydrogen peroxide containing part is prepared by mixing the same components as the disclosed example except the amount of hydrogen peroxide is 1% by weight. The corresponding amount of water is increased to 84% by weight. The amount of surfactant ingredients is kept the same.

The manganese dioxide nanoparticle containing part is also prepared following the example described in the patent above except the peroxide left out as ingredient and manganese dioxide nanoparticles are included. The manganese dioxide is added to the composition in the form of its concentrate prepared in Example 1. The amount of concentrate is adjusted to achieve ~100 ppm of manganese dioxide with the appropriate adjustment to the water added. The portions are contained in a 2 part dispenser disclosed above for subsequent use. The ratio of the two parts exiting the dispenser is maintained at 1:1 though other ratio also can be maintained.

Example 11

Base Solution as Emulsion (Prophetic)

An oil-in-water emulsion was prepared as per Example 2 of the U.S. Pat. No. 4,485,091 with few modifications as follows. The lactic acid component was left out and hydrogen peroxide amount of changed to 1% by weight. The hydrogen peroxide containing part is made incorporating these changes.

The manganese dioxide containing part is also made using the same base oil-in-water emulsion but with following changes. The lactic acid is omitted and aqueous manganese dioxide nanoparticles concentrate (from Example 1 of this application) is added in an amount that will yield ~100 ppm manganese dioxide. Finally water is added appropriate quantity to complete the mass balance and emulsion preparation.

The two parts are then packaged in a dual chamber pump dispenser for further use.

While the disclosure has been described in detail with respect to specific embodiments thereof, it will be apparent to those skilled in the art that various alterations, modifications and other changes may be made to the disclosure without departing from the spirit and scope of the present disclosure. It is therefore intended that the claims cover all such modifications, alterations and other changes encompassed by the appended claims.

We claim:

1. A two part spray for the liberation and delivery of oxygen for cosmetic formulations, the spray comprising a first part that includes a peroxide-containing solution and a second part that includes a nanoparticle manganese dioxide catalyst solution, wherein mixing the nanoparticle manganese dioxide catalyst solution with said peroxide containing solution results in the liberation of oxygen, wherein the spray is in the form of an aerosol, wherein the first part and the second part of the two part spray are stored in separate reservoirs of a container until liberation of oxygen is desired, further wherein the manganese dioxide nanoparticles have an average size between about 5 and 500 nanometers, are present in the catalyst solution at a concentration between 25 and 100 ppm, or a combination thereof.

2. The two part spray of claim 1, wherein said spray is aqueous, non-aqueous, or a mixture thereof.

3. The two part spray of claim 1, further comprising a natural or synthetic polymer, a moisturizer, a humectant, a viscosity modifier, an emollient, a texture enhancer, a UV blocking agent, a colorant, a pigment, a ceramic, an antioxidant, a fragrance, or a combination thereof.

4. The two part spray of claim 1, wherein the manganese dioxide nanoparticles have an average size between about 50 and 300 nanometers.

5. The two part spray of claim 1, wherein the second part may be a liquid, gel, foam or emulsion of oil in water or water in oil.

6. The two part spray of claim 1, wherein the concentration of manganese dioxide in the second part is between 25 and 100 ppm.

7. The two part spray of claim 1, wherein the concentration of manganese dioxide in the second part is between 75 and 100 ppm.

8. The two part spray of claim 1, wherein the concentration of hydrogen peroxide in the first part is from a positive amount to about 3 weight percent.

9. The two part spray of claim 1, wherein the spray is alkaline.

10. The two part spray of claim 1, wherein the manganese dioxide catalyst solution further comprises an additional catalyst.

11. The two part spray of claim 10, wherein the additional catalyst is sodium bicarbonate, calcium hydroxide, or a combination thereof.

12. A two part spray for the liberation and delivery of oxygen for cosmetic formulations comprising a first part that includes a peroxide-containing solution containing less than 3 weight percent hydrogen peroxide and a second part that includes a nanoparticle manganese dioxide catalyst solution, wherein said nanoparticles have an average size between about 50 and 300 nanometers and are present in the catalyst solution at a concentration between 25 and 100 ppm, wherein the first part and the second part of the two part spray are stored in separate reservoirs of a container until liberation of oxygen is desired, wherein the two parts, when mixed together as an aerosol, result in the liberation of oxygen.

13. The two part spray of claim 11, further comprising a natural or synthetic polymer, a moisturizer, a humectant, a viscosity modifier, a emollient, a texture enhancer, a UV blocking agent, a colorant, a pigment, a ceramic, an antioxidant, a fragrance, or a combination thereof.

14. The two part spray of claim 11, wherein the spray is alkaline.

15. The two part spray of claim 11, further comprising an additional catalyst.

16. The two part spray of claim 15, wherein the second catalyst is sodium bicarbonate, calcium hydroxide, or a combination thereof.

* * * * *